(12) United States Patent
Zankowski

(10) Patent No.: US 8,774,358 B2
(45) Date of Patent: Jul. 8, 2014

(54) RADIATION THERAPY TREATMENT PLAN IMPROVEMENT THROUGH USE OF KNOWLEDGE BASE

(75) Inventor: Corey Zankowski, San Jose, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 350 days.

(21) Appl. No.: 13/247,270

(22) Filed: Sep. 28, 2011

(65) Prior Publication Data

US 2013/0077752 A1 Mar. 28, 2013

(51) Int. Cl.
*A61N 5/10* (2006.01)

(52) U.S. Cl.
USPC .............................................. 378/65; 378/97

(58) Field of Classification Search
CPC ...................................................... A61N 5/103
USPC ............................................ 378/65, 97, 108
See application file for complete search history.

(56) References Cited

U.S. PATENT DOCUMENTS

2004/0190680 A1* 9/2004 Chang .............................. 378/65
2012/0014507 A1* 1/2012 Wu et al. .......................... 378/65

* cited by examiner

*Primary Examiner* — Hoon Song

(57) ABSTRACT

A radiation therapy dose distribution method starts with selecting a treatment type. Then an organ at risk (OAR) distance to target map is determined. The OAR distance to target map comprises distances to a target organ for portions of an OAR. The OAR distances are determined from at least one segmented patient organ image. A cohort average dose distance to target histogram is selected. A dose value to the portions of the OAR are assigned to form a first 3D dose distribution map. The dose values are from the selected cohort average dose distance to target histogram. A second 3D dose distribution map is determined based on a field arrangement determined by the treatment type and the first 3D dose distribution map. A dose distance to target histogram is calculated using the second 3D dose distribution map and the distance to target map.

30 Claims, 13 Drawing Sheets

Data Hierarchy

Data Hierarchy (abbreviated)

ical decisions is increasing non-linearly, resulting in a rapidly widening gap between actual practice and best practices, especially in emerging markets.

RADIATION THERAPY TREATMENT PLAN IMPROVEMENT THROUGH USE OF KNOWLEDGE BASE

TECHNICAL FIELD

The present disclosure relates generally to the field of radiation therapy and more specifically to the field of radiation therapy treatment plan development.

BACKGROUND

Oncology and Radiotherapy technology continues to evolve, accelerating the expansion of the envelope of possible treatments and best practices associated with those possible treatments. At the same time, the complexity of clinical decisions is increasing non-linearly, resulting in a rapidly widening gap between actual practice and best practices, especially in emerging markets.

For example, when medical imaging is necessary in the course of radiation therapy, several systems may be used, such as X-ray, magnetic resonance imaging (MRI), computed tomography (CT), and others. When CT or MRI imagery, for example, is used, a series of two-dimensional images are taken from a three-dimensional volume. Here, each two-dimensional image is an image of a cross-sectional "slice" of the three-dimensional volume. The resulting collection of two-dimensional cross-sectional slices can be combined to create a three dimensional image or reconstruction of the patient's anatomy. This resulting three-dimensional image or three-dimensional reconstruction will contain organs of interest. Those organs of interest include the organ targeted for radiation therapy, as well as other organs that may be at risk of radiation therapy exposure. The portion of the three-dimensional image or reconstruction that contains the organs of interest may be referred to as structures of interest or volumes of interest.

These one or more structures of interest may be viewed in several ways. A first and simplest way to view the structure(s) of interest would be to merely view the original CT or MRI image slices for the patient, with each slice containing a view of the structure(s) of interest. A second, and more complicated method to view the structure(s) of interest would be to combine the series of two-dimensional cross-sectional slices into a single three-dimensional representation where the structure(s) of interest may be represented as solid, opaque, or translucent, etc., objects that may then be manipulated (e.g., rotated) to allow viewing from multiple angles.

One purpose of the three-dimensional reconstruction of the structure(s) of interest containing diseased or abnormal tissues or organs is the preparation of a three-dimensional radiation therapy treatment plan. Radiation therapy treatment plans are used during medical procedures that selectively expose precise areas of the body, such as cancerous tumors, to specific doses of radiation to destroy the undesirable tissues. To develop a patient-specific radiation therapy treatment plan, information is extracted from the three-dimensional model to determine perimeters such as organ shape, organ volume, tumor shape, tumor location in the organ, and the position or orientation of several other structures of interest as they relate to the affected organ and any tumor.

The two-dimensional slices may be individually viewed on a computer screen and with the use of conventional graphics programs, the contours of organs or structures of interest can be traced out by hand. Contours are connected line segments that define the outline of a structure of interest, which may be an organ, a portion of an organ, a tumor, diseased tissue, or a whole patient outline. Alternatively, these structures of interest in specific organs such as the brain or prostate, for example, may be identified with various structure-specific automatic contouring and/or automatic segmentation software programs (subdividing an image into discrete regions) that outline or fill the shape of the structure of interest on each two-dimensional slice of a set of slices.

As evolving technologies provide increasingly complicated radiation therapy treatment planning possibilities, the gap between actual clinical practice in treatment planning and possible best practices in treatment planning increases. Therefore improved methods for realizing and communicating improved results using emerging technological innovations are required.

SUMMARY OF THE INVENTION

This present invention provides a solution to the challenges inherent in achieving radiation therapy treatment planning best practices. In a method according to one embodiment, a series of steps provide for an improved radiation therapy dose distribution. A method for generating a radiation therapy dose distribution plan starts with selecting and downloading a treatment type from a database. Then an organ at risk (OAR) distance to target map is determined, wherein the OAR distance to target map comprises distances to a target organ for respective portions of at least one OAR, and wherein the OAR distances are determined from at least one segmented patient organ image. Now a cohort average dose distance to target histogram is selected and downloaded from the database. After which, a dose value to the portions of the at least one OAR are assigned to form a first 3D dose distribution map, wherein the dose values are from the selected cohort average dose distance to target histogram. Now a second 3D dose distribution map is determined based on a field arrangement determined by the treatment type, and the first 3D dose distribution map. The second 3D dose distribution map can now be optimized to generate a third 3D dose distribution map. Finally, a dose distance to target histogram is calculated for the patient using the third 3D dose distribution map and the distance to target map.

BRIEF DESCRIPTION OF THE DRAWINGS

The present invention will be better understood from a reading of the following detailed description, taken in conjunction with the accompanying drawing figures in which like reference characters designate like elements and in which.

DETAILED DESCRIPTION

Figure 1:
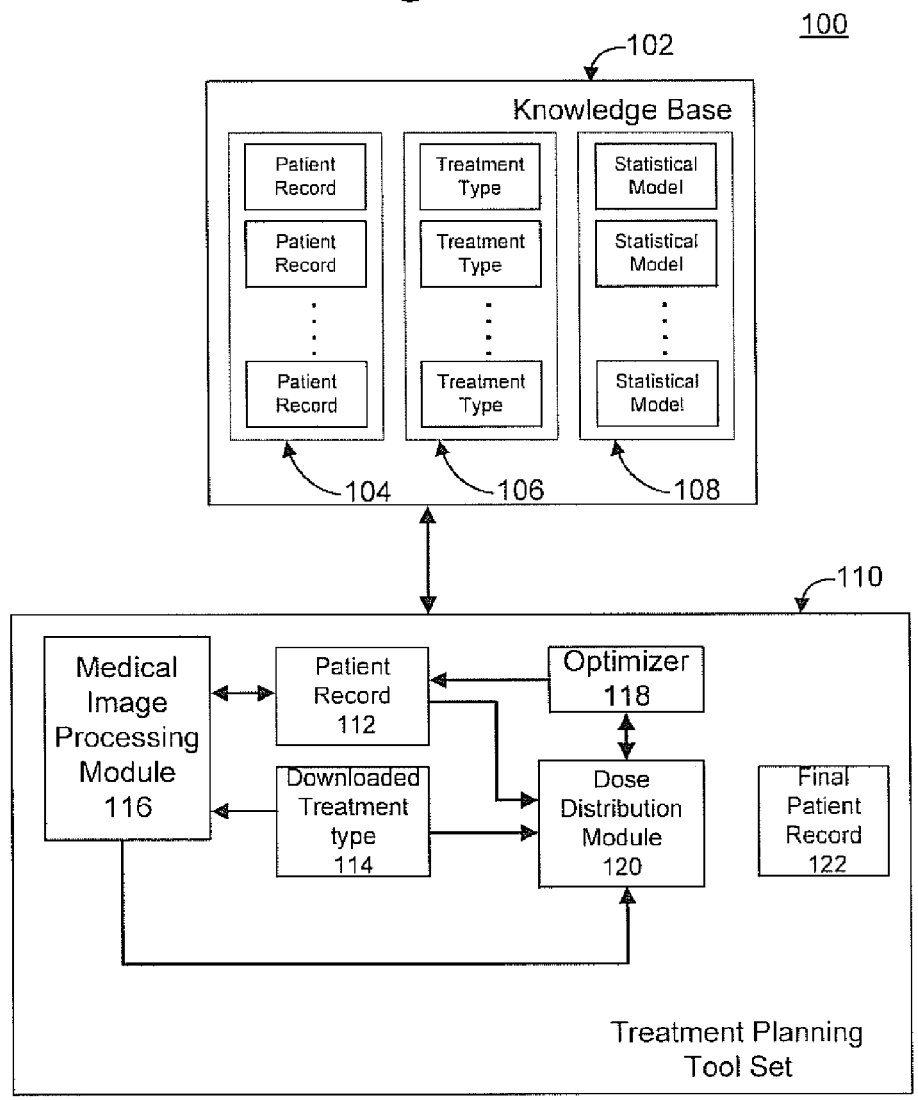
FIG. 1 is a simplified block diagram illustrating an embodiment of a knowledge-based treatment planning system, in accordance with an embodiment of the present disclosure.

Reference will now be made in detail to the preferred embodiments of the present invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of embodiments of the present invention, numerous specific details are set forth in order to provide a thorough understanding of the present invention. However, it will be recognized by one of ordinary skill in the art that the present invention may be practiced without these specific details. In other instances, well-known methods, procedures, components, and circuits have not been described in detail so as not to unnecessarily obscure aspects of the embodiments of the present invention. The drawings showing embodiments of the invention are semi-diagrammatic and not to scale and, particularly, some of the dimensions are for the clarity of presentation and are shown exaggerated in the drawing Figures. Similarly, although the views in the drawings for the ease of description generally show similar orientations, this depiction in the Figures is arbitrary for the most part. Generally, the invention can be operated in any orientation.

Notation and Nomenclature:

Some portions of the detailed descriptions, which follow, are presented in terms of procedures, steps, logic blocks, processing, and other symbolic representations of operations on data bits within a computer memory. These descriptions and representations are the means used by those skilled in the data processing arts to most effectively convey the substance of their work to others skilled in the art. A procedure, computer executed step, logic block, process, etc., is here, and generally, conceived to be a self-consistent sequence of steps or instructions leading to a desired result. The steps are those requiring physical manipulations of physical quantities. Usually, though not necessarily, these quantities take the form of electrical or magnetic signals capable of being stored, transferred, combined, compared, and otherwise manipulated in a computer system. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present invention, discussions utilizing terms such as "processing" or "accessing" or "executing" or "storing" or "rendering" or the like, refer to the action and processes of a computer system, or similar electronic computing device, that manipulates and transforms data represented as physical (electronic) quantities within the computer system's registers and memories and other computer readable media into other data similarly represented as physical quantities within the computer system memories or registers or other such information storage, transmission or display devices. When a component appears in several embodiments, the use of the same reference numeral signifies that the component is the same component as illustrated in the original embodiment.

This present disclosure provides a solution to the increasing challenges inherent in improving radiation therapy best practices. In particular, various embodiments of the present disclosure provide the use of a knowledge base incorporating a mixture of patient records and statistical models to simplify the generation of new reasonably optimized radiation therapy dose distribution treatment plans. As discussed in detail below, the new radiation therapy treatment plans, and their dose distributions, are based on prior clinical experience. Further, as also discussed in detail below, after each new treatment plan is generated, the resulting treatment plan is used to dynamically update statistical models of the radiation therapy planning process such that the system can self-learn and improve with each new patient. By using statistical models based on prior treatment plans approved by the clinician, as well as selecting a most commonly used treatment type, based on the current patient's meta-data, embodiments are able to create "reasonably good" treatment plans that can be easily optimized by the system and refined by the clinician, such that the clinician's refinements are used to update the statistical models.

As discussed in detail below, embodiments of the present disclosure generate radiation therapy dose distribution plans by selecting a treatment type from the knowledge base. An appropriate treatment type is selected based on a review of a current patient record's meta-data. With the determination of the appropriate treatment type, appropriate beam geometry is also selected. In parallel with the selection of a treatment plan and beam geometry, the nearest distance to the target organ for each pixel in the medical image is calculated to create a distance to target map. Such calculation may be performed immediately after organ segmentation is completed and approved by the clinician.

Next the distance to target map, the patient meta-data and selected treatment type are used to determine which patient cohort the current patient is a part of. A cohort average distance to target histogram is downloaded from the knowledge base. The cohort average distance to target histogram is used to assign a dose value to every pixel in the medical image, such that each structure (e.g. organ) is populated with dose values. Now the beam geometry and the assigned dose distribution are used to compute a set of fluences and a 3D dose distribution map. The set of fluences are computed such that they will minimize the differences within the assigned dose distribution, while providing more dose to the target organ and less dose to the organs at risk.

Next the knowledge base will be searched for a combination of optimization objectives that can be applied by an optimizer to optimize the dose distribution. For example, an average organ at risk dose volume histogram, a mean cohort organ at risk dose volume histogram and average organ at risk objectives are selected from the knowledge base. In one embodiment, there are a plurality of organs at risk with associated average organ at risk dose volume histograms and cohort average organ at risk dose volume histograms. In other words, the optimizer will have an objective of at least meeting the average dose distribution achieved previously in similar patients by the clinician. As described in detail below, the optimizer may make use of 2D penalty maps to help shape the dose distribution such that doses received by one or more critical organs at risk are minimized and the dose to the target organ is maximized. Other objective functions may include biological outcome maps and a dose distance to target histogram. Using the objectives and field arrangement, the optimizer will provide an optimal 3D dose distribution, fluences and associated dose volume histograms for the current patient. Optimally, these results will fall within the historically accepted range for a patient with a similar disease type and treatment type.

In further steps, the clinician can review the results of the optimization and adjust optimization parameters. By changing the objectives, the clinician can drive the optimizer to a new result. The new objectives are appended into the patient organ at risk objective functions. The resulting new dose distribution, fluence and dose volume histogram are also stored in the patient record. Once the clinician is satisfied with the final result and having verified that all treatment plan elements are consistent, a dose distance to target histogram is calculated for the current patient. Finally, the knowledge base can be updated with the current patient information. After determining which population cohort the current patient belongs in, the field geometry is updated for the selected cohort, while population statistics and the cohort population statistics are also updated with the new data.

An exemplary radiation therapy treatment planning system 100, as illustrated in FIG. 1, comprises a knowledge base 102 and a treatment planning tool set 110. The knowledge base 102 of FIG. 1 comprises a plurality of patient records 104, a plurality of treatment types 106, and a plurality of statistical models 108. The treatment planning tool set 110 of FIG. 1 comprises a current patient record 112 (e.g., comprising an incomplete treatment plan), a downloaded treatment type 114, a medical image processing module 116, an optimizer 118, a dose distribution module 120, and a completed patient record 120 (e.g., comprising a final, approved treatment plan). As discussed in detail below, the treatment planning tool set searches through the knowledge base for prior patient records that are similar to the current patient case, and using current patient information, a selected treatment type 106, and selected statistical models 108, generates a treatment plan in the patient record 112.

As discussed in detail below, the treatment planning system 100 has an objective to create a "reasonably good" treatment plan that the clinician can optimize to create an acceptable final treatment plan. In an exemplary embodiment, the treatment planning system 100 will search for similar patient records 104 and matching treatment types 106 that were created by the clinician for other patients. Using only previous patient records 104, treatment types 106, and statistical models 108 based on those same patient records 104 and treatment types 106 that were previously created and approved by the clinician can provide the "reasonably good" treatment plans that are based upon what the clinician has approved in the past. In another embodiment, a cohort sample can comprise previous patient records 104, treatment types 106, and their corresponding statistical models 108 for several clinicians, for example, a group of clinicians in a clinic. In a further embodiment, the cohorts can be further segmented to contain only those previous patient records 104, treatment types 106, and corresponding statistical models 108 that had good outcomes as determined by the clinician.

Figure 2A:
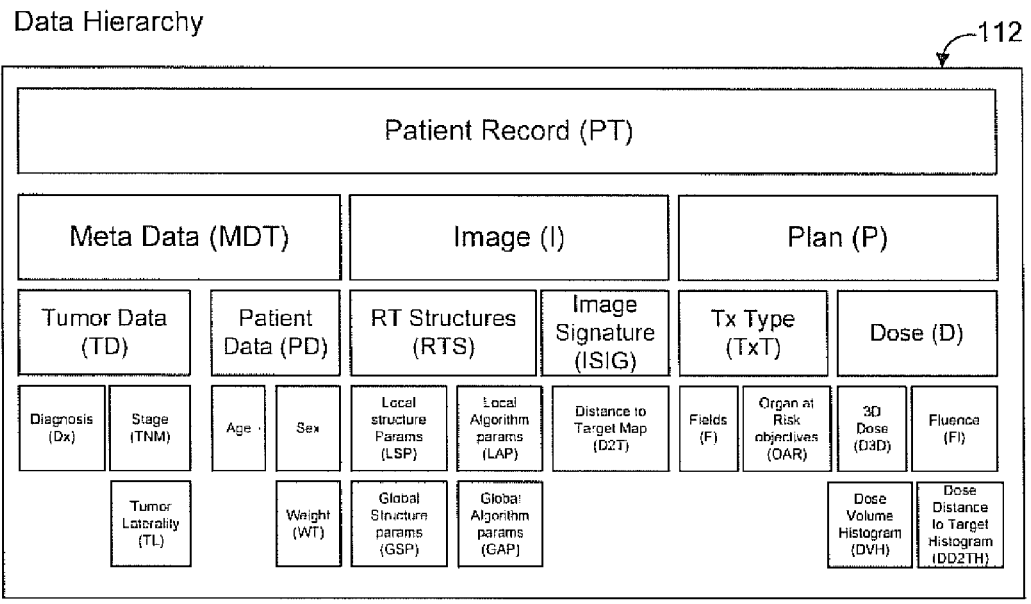
FIGS. 2A and 2B are simplified block diagrams illustrating the data hierarchy for a patient record that is part of a treatment plan, in accordance with an embodiment of the present disclosure.
Figure 2B:
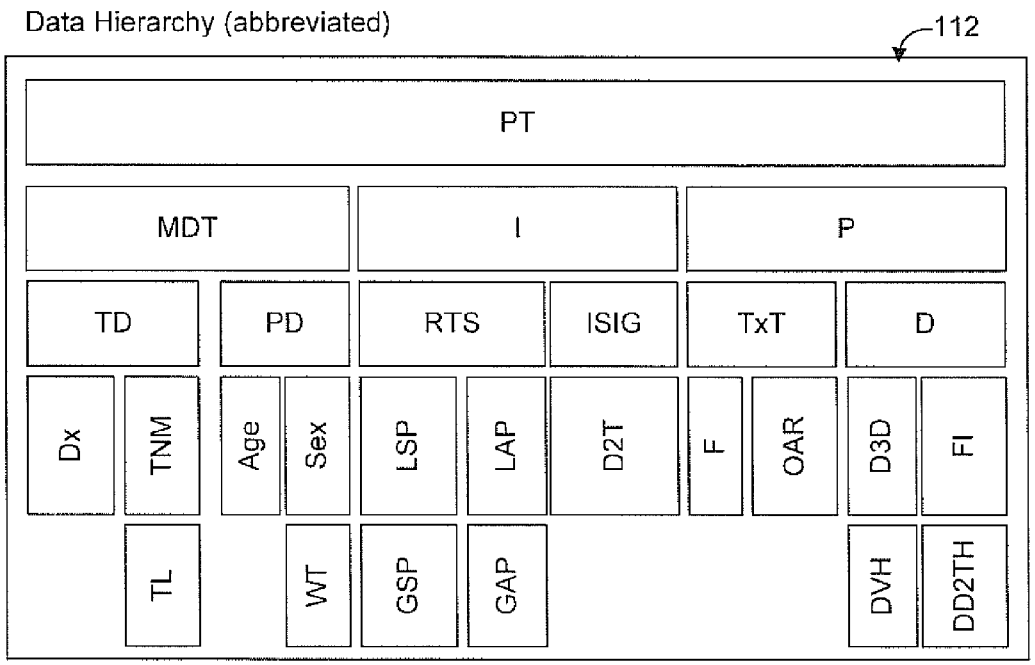

As illustrated in FIGS. 2A and 2B, the current patient record 112 has a hierarchy, wherein patient information in the patient record 112 comprises for instance Meta Data (MDT), Medical Images (I), and a Treatment Plan (P). The Meta Data (MDT) comprises Tumor Data (TD), a Diagnosis (Dx), Stage (TNM), Tumor Laterality (TL), Patient Data (PD), Age, Sex, and Weight (WT). The Images (I) comprise RT Structures (RTS), Image Signature (ISIG), Local Structure Parameters (LSP), Local Algorithm Parameters (LAP), Distance to Target (D2T), Global Structure Parameters (GSP), and Global Algorithm Parameters (GAP). Lastly, the Treatment Plan (P) comprises a Treatment Type (TxT), a Dose (D), Fields (F), Organ at Risk Objectives (OAR), a 3D Dose map (D3D), Fluences (FL), Dose Volume Histogram (DVH), and a Dose Distance to Target Histogram (DD2TH). For the sake of clarity in the following Figures, the element names of FIG. 2A are abbreviated as illustrated in FIG. 2B.

Figure 3:
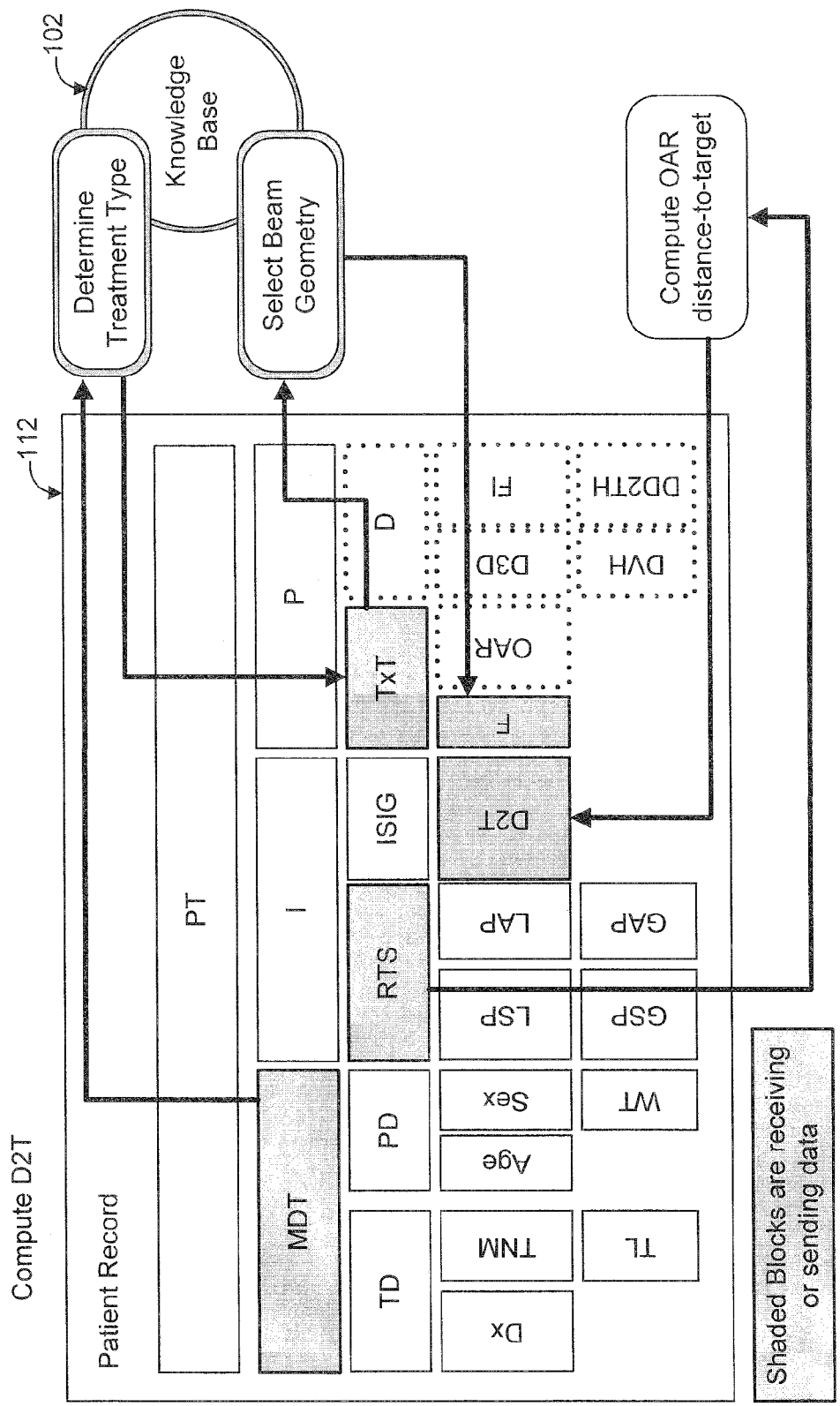
FIGS. 3-6 are simplified block diagrams illustrating an embodiment of a knowledge-based treatment planning system, in accordance with an embodiment of the present disclosure.

As illustrated in FIG. 3, the process begins with an incomplete patient record 112. The faded portions on the lower right-hand corner of the patient record 112 are those portions that have not yet been populated with data. The shaded blocks are those elements that are receiving or sending data. The rounded boxes (e.g., "Determine Treatment Type" and "Select Beam Geometry") represent an execution or logical step that is currently being performed. Further, the rounded boxes with shading around them are those execution or logical steps currently being performed that are selecting data from the knowledge base 102.

As further illustrated in FIG. 3, the current patient's metadata (MDT) is used to search the knowledge base 102 for a suitable treatment type. Based on past clinical experience, when a patient presents with a particular diagnosis, stage, age, weight, sex, co-morbidities, etc., there can be a treatment type that is used most often. By selecting the treatment type that the clinician has used in the past for similar patients, a first step, "most popular" treatment type 114 can be chosen. As further illustrated in FIG. 3, when a treatment type 114 is selected and downloaded into the patient record 112, a beam geometry that determines a field arrangement can be selected from the knowledge base 102 and stored in the patient record 112. The field arrangement is also a driver of a dose distribution. What the clinician is able to achieve is in part determined by the selected beam geometry. For example, a 4-field box using four beams coming at each other to form a box, will have a dose distribution shaped like a box. Other techniques, such as 3D conformal mapping, etc., will each have a different predictable result.

The medical image processing module 116 provides automatic contouring and automatic segmentation of each of the two-dimensional cross-sectional slides used in forming a three dimensional image with the medical images in the medical record 112. Such segmentation and contouring of the medial images in the patient record 112 is discussed by Zankowski, in pending U.S. patent application Ser. No. 12/845,358, filed Jul. 28, 2010, entitled "KNOWLEDGE-BASED AUTOMATIC IMAGE SEGMENTATION," which is incorporated herein by reference. Once the medical images in the patient record have been segmented, the segmented structures of interest (e.g., organs) can be used to compute an organ at risk distance to target map (D2T). In creating the organ at risk distance to target map (D2T), each pixel of each segmented image, of the plurality of two-dimensional cross-sectional slides, is assigned a value that is a determined minimum distance to the target organ for the respective pixel. The distance to target map (D2T) is created and placed into the patient record. There is an "inside" and an "outside" for a target volume. Everything inside the target volume (e.g., inside the target organ that is to receive the prescribed radiation therapy dose) is assigned a negative value, the surface of the target volume is assigned as "zero" and everything outside the target volume is computed for the shortest distance from individual pixels to the target volume.

Figure 4:
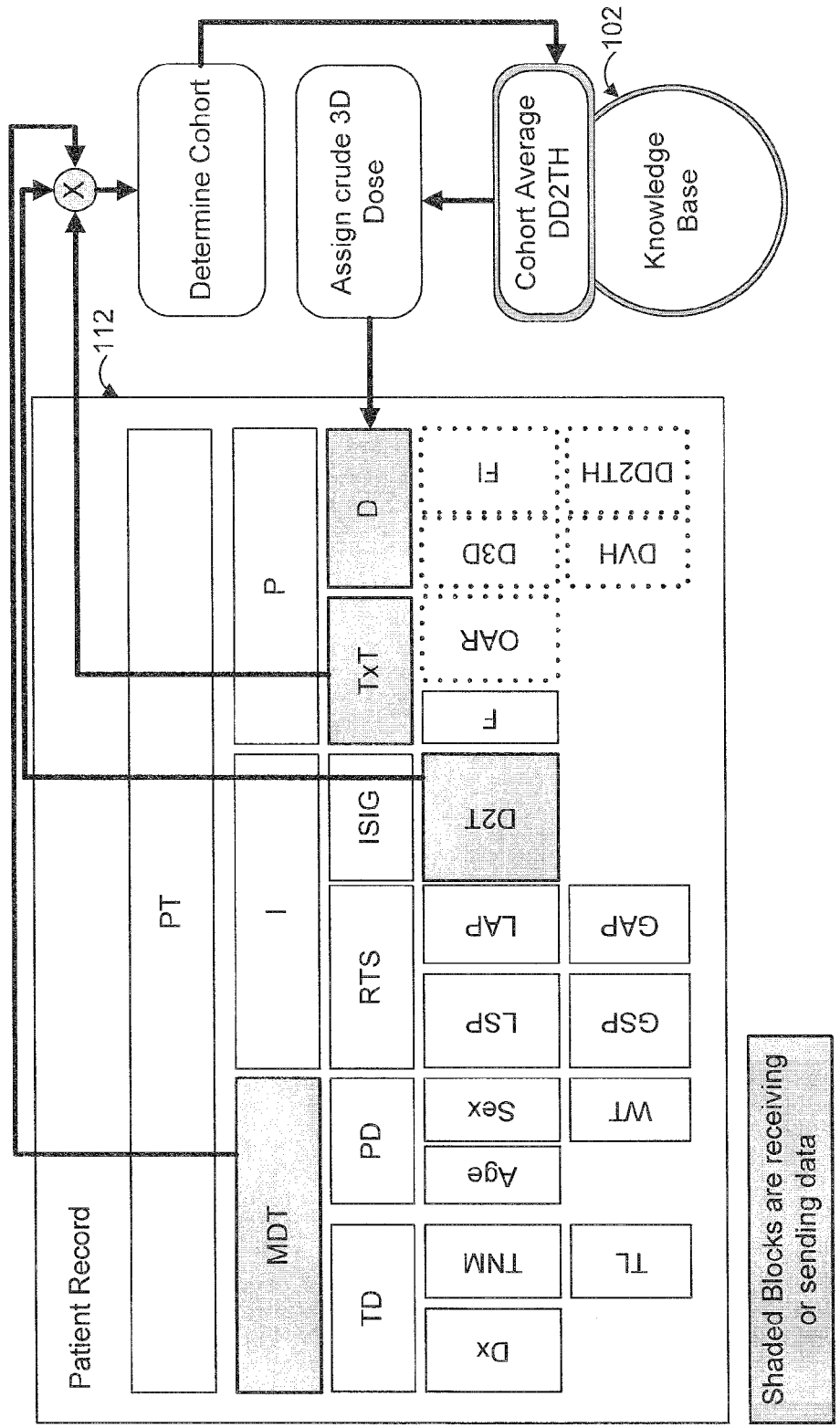

As illustrated in FIG. 4, the patient's meta-data (MDT), the distance to target map (D2T), and the treatment type 114 are used together to determine a population cohort that the current patient is a member of. Once the population cohort is selected, a cohort average dose distance to target histogram (DD2TH), for the selected cohort, is selected and downloaded. While the distance to target map (D2T) is a "signature" of the patient's segmented structures, the cohort average dose distance to target histogram (DD2TH) is a signature of the selected treatment technique 114. Because such a signature from the selected treatment technique 114 is dependent on beam orientation, only those dose distance to target histograms (DD2TH) using the same treatment technique (which make up the selected population cohort) will be used in determining the selected cohort average dose distance to target histogram. In other words, there are different characteristic dose distributions for each field arrangement, such that a 5-field treatment will have a different characteristic dose distribution than a 3-field or a 9-field treatment. In a further embodiment, when the cohort population is sufficiently sized, the cohort can be further refined by selecting patient records from the cohort who have similar distance to target characteristics to the current patient to create a more refined cohort and associated cohort average dose distance to target histogram (DD2TH).

As further illustrated in FIG. 4, once a cohort average dose distance to target histogram (DD2TH) has been selected and applied to the current patient's treatment plan 112, a crude 3D dose distribution (D) can be calculated. In one embodiment, the crude 3D dose distribution (D) is generated by the dose distribution module 120 of the treatment planning tool set 110. In additional embodiments, all dose distribution maps are calculated by the dose distribution module 120 of the treatment planning tool set 110. The crude 3D dose distribution map is generated by using the selected cohort average dose distance to target histogram (DD2TH) to assign a dose value to every pixel in the patient images separately for each structure and for generic normal tissue. After the crude 3D dose distribution (D) is calculated, this 3D dose distribution (D), as illustrated in FIG. 4, is stored in the patient record. In another embodiment, dose values can be assigned to pixels only within the primary beam or throughout the images.

The crude 3D dose distribution map (D) applies an amount of dose to the organs at risk as a function of their distance to the target. In other words, a pixel x-distance from the target organ is assigned a particular y-quantity of dose. In another embodiment, areas of the images that are not specified at the organ level can be lumped into a radial dose. Because these unspecified portions would otherwise just be holes in the map, they can be lumped together. In establishing this first crude 3D dose distribution (D), the clinician may chose a certain confidence level.

In an exemplary embodiment, after completing the preliminary analysis, there are for example, 100 patients in the knowledge base that are members of the selected cohort. Therefore, when an exemplary confidence level of 95% is selected 5% or 5 patients out of the 100 patients will have doses that are higher than the average dose distribution for the particular treatment technique. When a clinician assigns a confidence level they are also setting an objective, or a starting point for the optimizer. Therefore, in one embodiment, the clinician may select conservative objective values (which are more difficult for the optimizer to solve) for the critical organs at risk and for less critical organs or areas in the desired distribution map that are not very well specified (e.g., areas outside the target organ and outside the critical organs at risk), a more relaxed dose limit can be selected. Such a combination of conservative dose objectives and relaxed dose objectives prevent the optimizer from unnecessarily reducing the dose levels.

Figure 5:
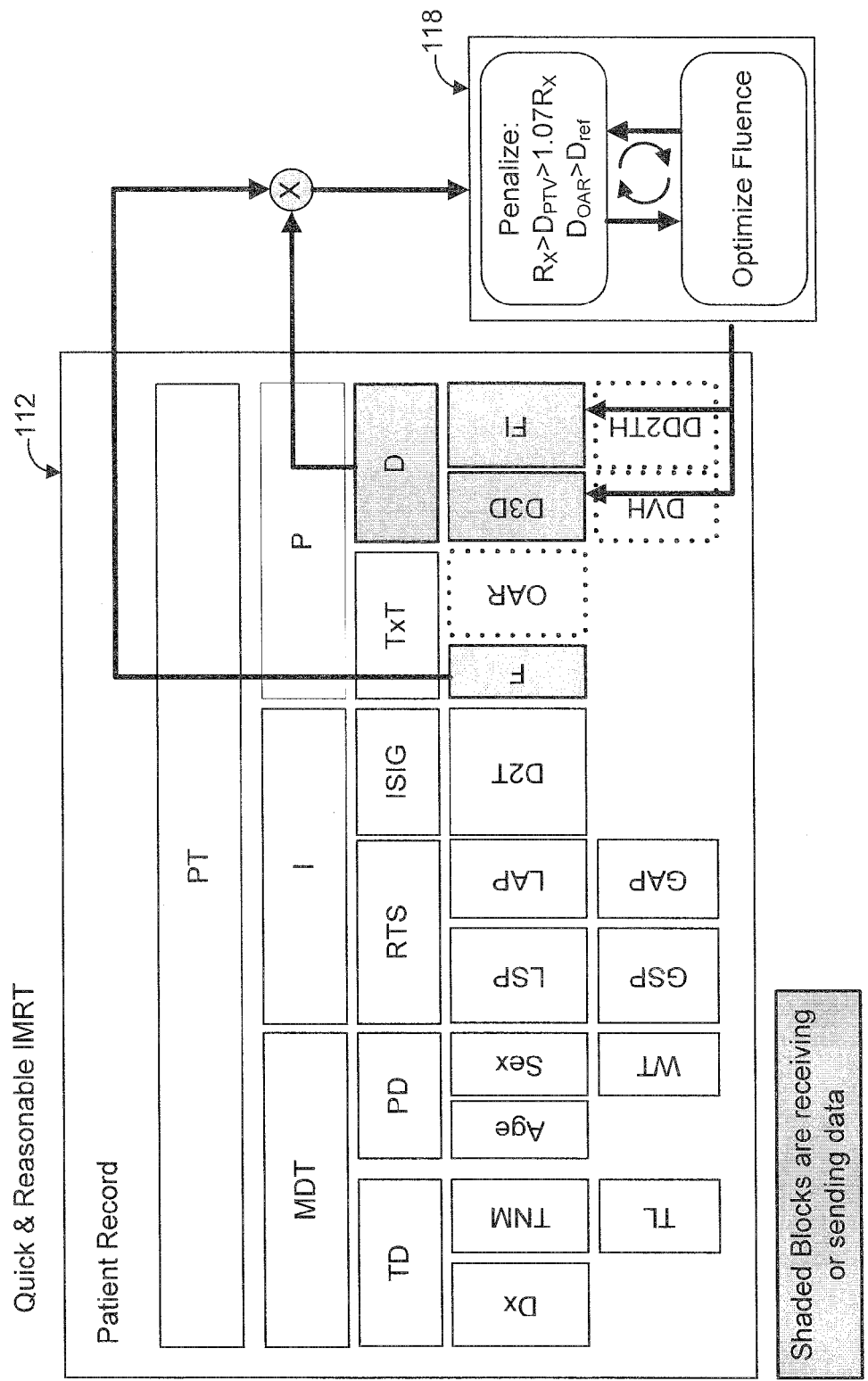

As illustrated in FIG. 5, the field arrangements (F) and the crudely assigned 3D dose distribution (D) are fed into the optimizer 118. The optimizer 118 will calculate a set of fluences (IMRT beamlettes) that will provide a reasonable 3D dose distribution (D3D). As illustrated in FIG. 5, the calculated 3D dose distribution (D3D) and fluences (FI) are stored in the patient record. The 3D dose distribution (D3D) results in a 3D model of the dose distribution. In other words, it will present a 3D model of the dose distribution with a particular dose for each pixel. In an exemplary embodiment, the optimizer 118 begins with a desired dose distribution and generates a set of fluences (FI) and resulting 3D dose distribution (D3D) that will as closely as possible match that desired dose distribution. While the desired dose distribution may have areas that are not physically achievable, the optimizer can smooth them out and provide the clinician a reasonable dose distribution that is achievable. This reasonable 3D dose distribution (D3D) provides a starting point for further optimization and adjustment by the clinician.

As further illustrated in FIG. 5, and discussed in detail below, the optimizer 118 may use 2D penalty maps to achieve a desired dose distribution. Using 2D penalty maps, the dose within the target volume, in one embodiment, is maintained at greater than or equal to the prescription, but not exceeding the prescription by more than, say 7%, while the dose within an organ at risk is set to not exceed an organ at risk dose distribution assigned from the cohort average dose distance to target histogram. As discussed above, exemplary embodiments comprise one or more organs at risk.

Figure 6:
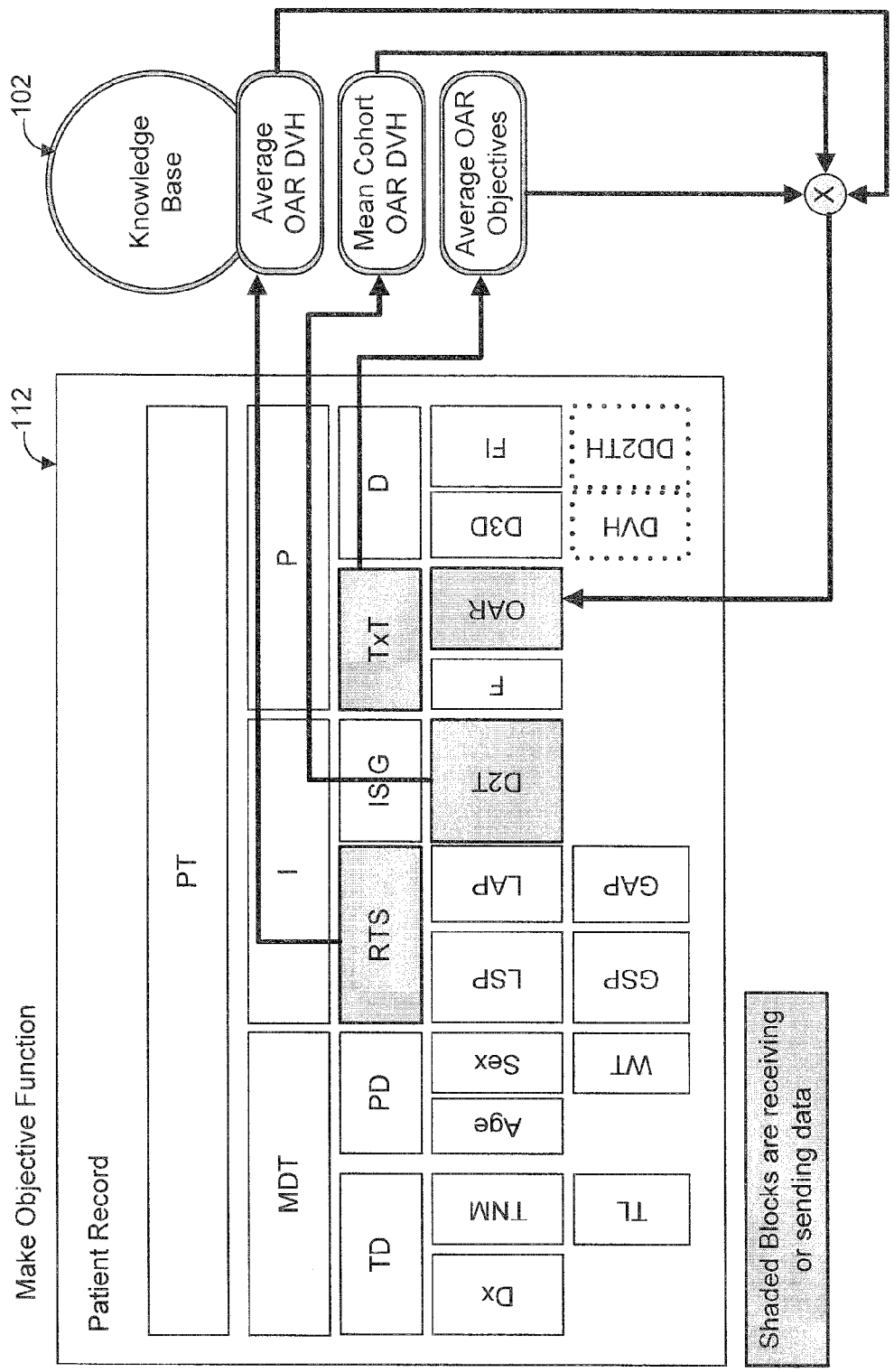

As illustrated in FIG. 6, the RT structures (RTS), the distance to target map (D2T), and treatment technique 114 in the current patient record 112 are used to select an average organ at risk dose volume histogram (OAR DVH), a mean cohort organ at risk dose volume histogram (OAR DVH) and average organ at risk objectives (OAR Objectives), respectively, from the knowledge base 102 to be fed into the optimizer 118 for each of the one or more organs at risk. By taking an average of the organ at risk dose volume histograms (OAR DVH) for the population and selected cohort population, the optimizer 118 may use an objective or goal that is based upon an average of the results achieved by the clinician while treating previous patients. In another embodiment, additional objectives may also be selected, such as biological models and a dose distance to target histogram. A biological model can estimate or predict the biological outcome that may result from a given dose distribution. The above objectives are combined to create a patient-specific organ at risk objective function (OAR) that is stored in the patient record 112. The organ at risk objective function (OAR) provides a goal for the optimizer 118 to reach for. As discussed above, based on the supplied organ at risk objective function (OAR), the optimizer 118 produces a set of fluences (FI) and a 3D dose distribution (D3D) that comes closest to meeting those assigned objectives for the target organ and the one or more organs at risk.

In an exemplary embodiment, the average, accepted, organ at risk dose volume histogram (OAR DVH) for each organ is selected. Using an average organ at risk dose volume histogram (OAR DVH) for each organ at risk is a reasonable request for the optimizer 118 to achieve. The average organ at risk dose volume histogram (OAR DVH) creates a statistical model 108 of the dose volume histograms that have been approved by the clinician in the past. In other words, a model is created for each organ at risk that is an average dose volume histogram.

Figure 7:
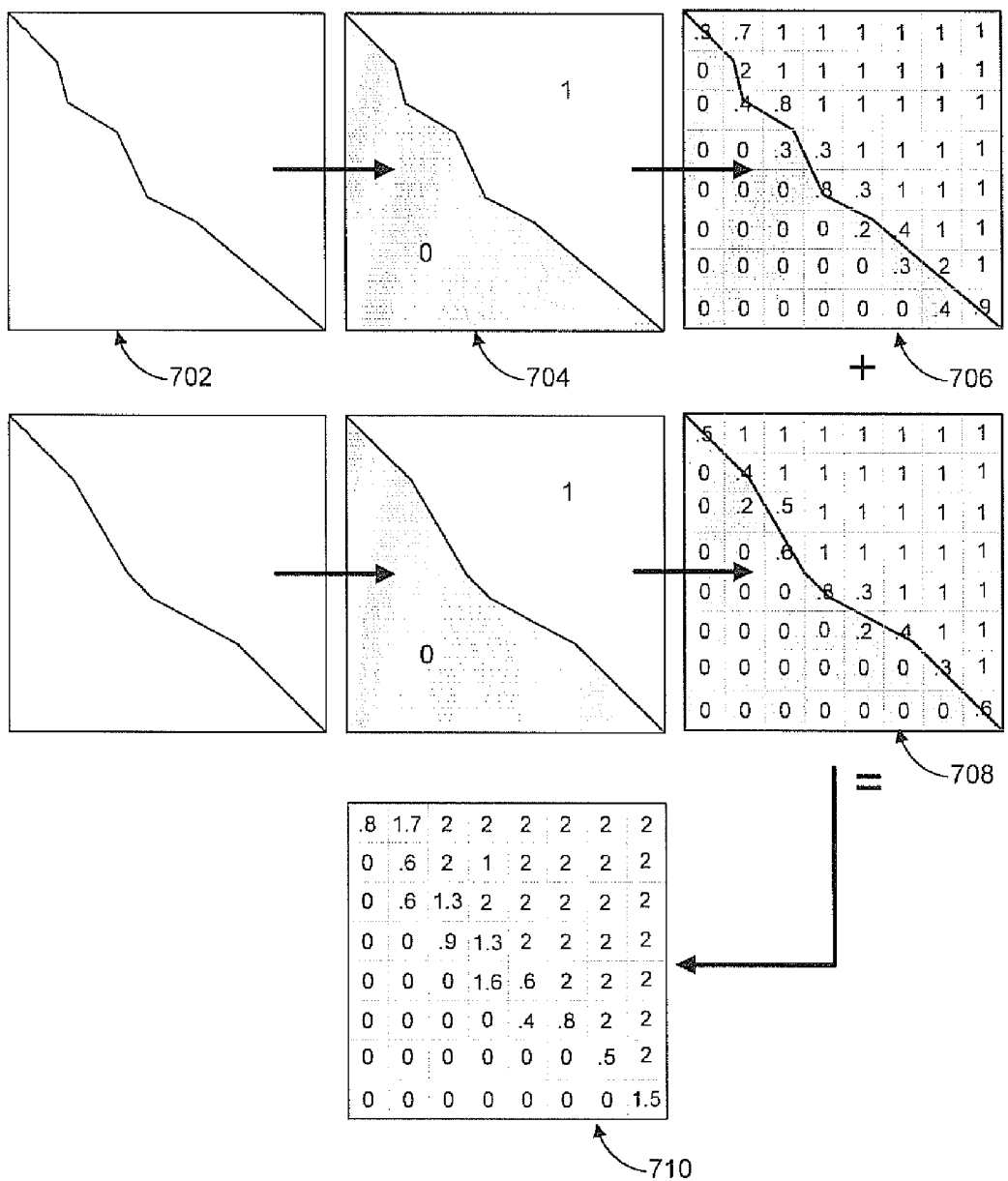
FIG. 7 illustrates the steps to the formation of a 2D penalty map using dose volume histograms, in accordance with an embodiment of the present disclosure.
Figure 8A:
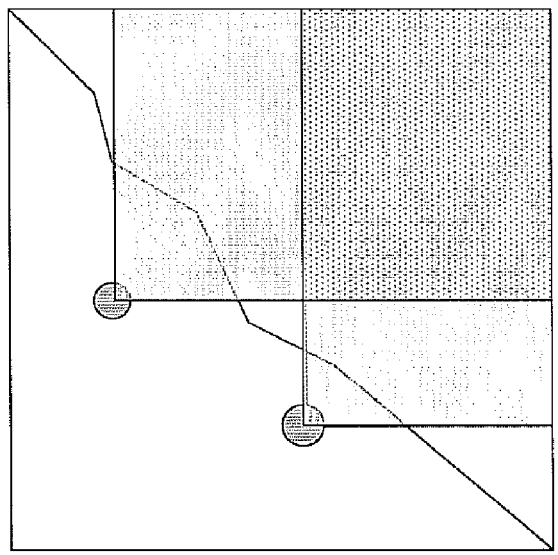
FIGS. 8A and 8B illustrate the steps to the conversion of dose volume histogram objectives into a 2D organ at risk penalty map, in accordance with an embodiment of the present disclosure.
Figure 8B:
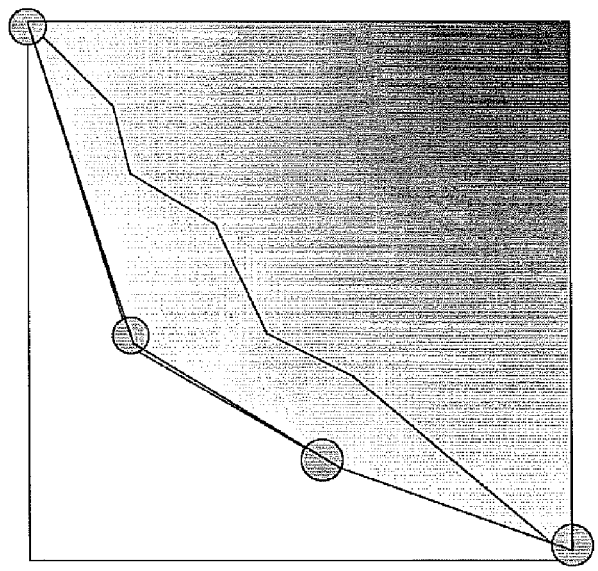

As illustrated in FIGS. 7, 8A, and 8B, the organ at risk histograms may be combined to create a 2D penalty map. Using the determined dose and volume from the averaged histograms, the objectives can be combined into a 2D matrix to simplify the optimizer task. The 2D penalty matrix will establish where and how the dose volume histogram curve flows through the penalty map.

As is well understood in the art, a dose volume histogram for an organ at risk may be broken down into a volume and a dose with a y-axis for the volume, and an x-axis for the dose. In a dose volume histogram 702, as illustrated in FIG. 7, at zero dose, 100% of the volume has received zero dose. As the dose increases, less and less of the organ will receive the increased dose amount. However, it is understood that in a target volume, the result will be the opposite. In a dose volume histogram for the target volume, it is desirable that 100% of the dose hits 100% of the target organ. In an exemplary embodiment, the dose to the target organ may be limited to, for example, 107% of the dose prescription. So for the target volume (e.g., target organ), the dose volume histogram curve may be pushed up to the top right of the histogram, while an organ at risk dose volume histogram curve 702, as illustrated in FIG. 7, may be pushed to the bottom left. This allows the majority of an organ at risk to have received as little dose as possible.

In one embodiment, an organ at risk dose volume histogram 702 may be converted into a 2D penalty matrix 704, 706. The 2D penalty matrix 704, 706 is formed through the use of a transfer function that converts what was successfully achieved in the past (an average dose volume histogram) into a 2D penalty map 704, 706. The transfer function uses an algorithm to convert the average dose volume histogram values into penalty values as illustrated in the 2D penalty map 704, 706, illustrated in FIG. 7. The values illustrated in the 2D penalty map 706 are exemplary in nature and may be different based upon different algorithms. In one embodiment, the 2D penalty map 704, 706 comprises values of zero (0) for dose levels below the curve and values of one (1) when above the curve, with those values lying on the curve receiving some fraction of the maximum value (e.g., 0.3, 0.8, and 0.4). In another embodiment the penalty values or weights may be assigned by multiplying the dose volume histogram matrix with a weighting factor.

In one embodiment, the penalty function can be set with values that will assign higher penalties when risks and consequences increase for those areas. Thus, higher penalty values can keep the optimizer 118 from allowing the dose to reach undesirable levels for critical areas. In other words, should a dose histogram curve attempt to place the curve through a penalty area with a high penalty value, the optimizer 118 will push the curve down and out of the high penalty area. The 2D penalty map 706 must therefore tradeoff between allowing a dose distribution that adequately places the dose in the target organ but minimizes the dose distribution in the organs at risk. In other words, there is a competition between ensuring adequate target organ coverage while simultaneously avoiding exposure to each of the organs at risk. Further, in other embodiments, the flexibility of the penalty function allows the dose distribution curve to drift into low-risk penalty areas while avoiding high-risk penalty areas to ensure adequate dose distribution. The low-risk and high-risk penalty areas represent those portions of the dose volume histogram where even low dose levels should be avoided (high-risk) as opposed to those areas where moderate dose levels can be tolerated (low-risk). Such areas are established by the clinician and will be represented in the average dose volume histograms.

In a further embodiment, the 2D penalty maps 706 of each previous dose volume histogram 708 (generated while treating previous patients of the selected population cohort) may be combined into an aggregate 2D penalty map 710 which will provide a more accurate and finely detailed penalty function taking into account the 2D penalty values for each of the previous 2D penalty maps 706, 708 of each patient record in a population cohort.

In another embodiment, dose volume histogram objectives may be converted to a 2D penalty map for each of the organs at risk, as illustrated in FIG. 8B. FIG. 8A illustrates a 2D penalty map penalizing a quadrant emanating from the dose objective, such that each point has its own penalty quadrant. The penalty values of FIG. 8A are computed as a line integral of the dose volume histogram through the summed penalty map ($P_j = w_j(D-D_j)^2$). In contrast to the method illustrated in FIG. 8A, the dose volume histogram objectives may also be converted to a 2D penalty map, as illustrated in FIG. 8B. The 2D penalty map illustrated in FIG. 8B results in a smoother penalty map than that illustrated in FIG. 8A. The objective points are connected with a straight line. Points are extrapolated from (O, 100) to (100, 0). Weights to the points are further interpolated along the line. Finally, penalty points are assigned based on a shortest distance to the curve.

Figure 9:
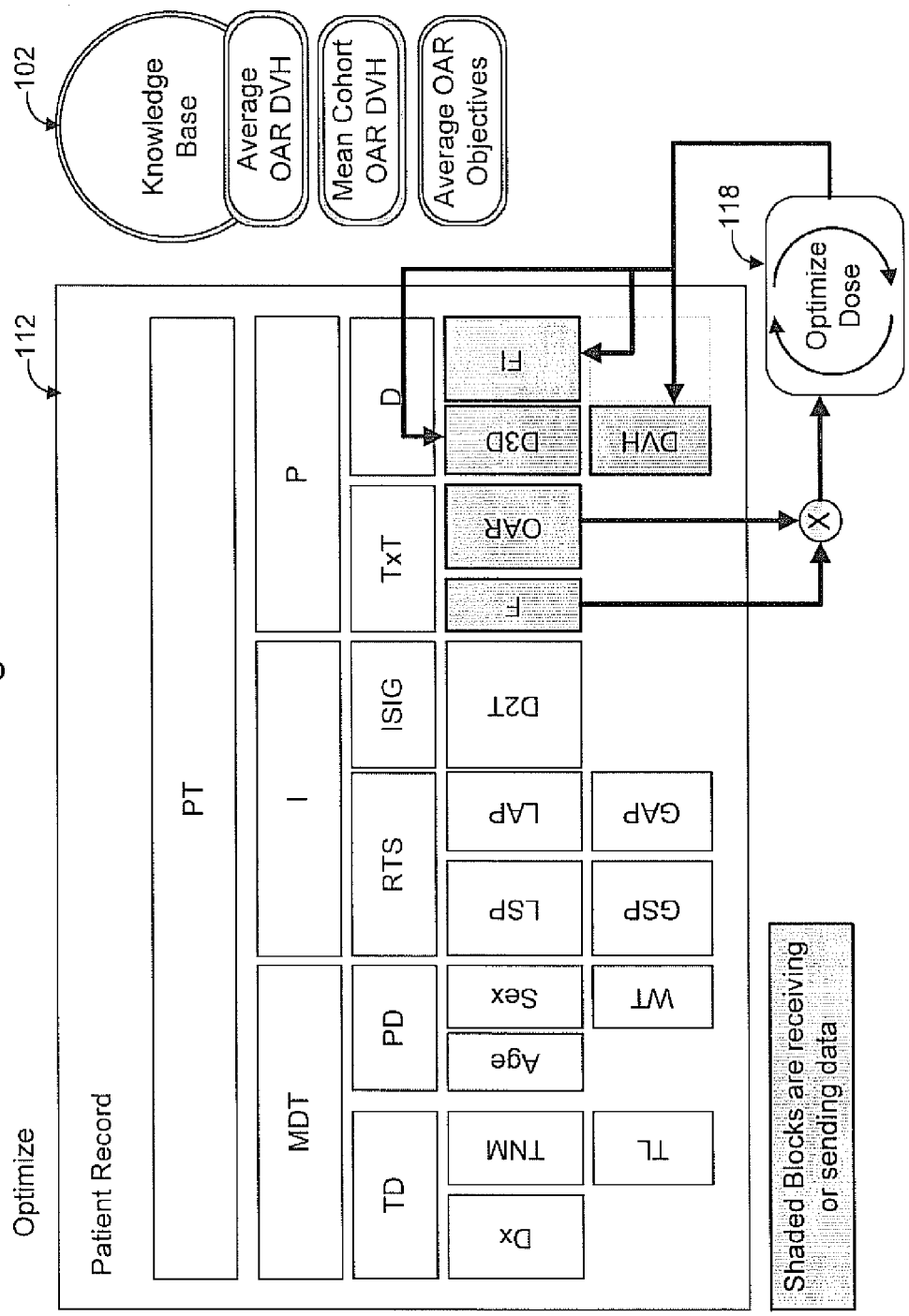
FIGS. 9-12 are simplified block diagrams illustrating an embodiment of a knowledge-based treatment planning system, in accordance with an embodiment of the present disclosure.

As illustrated in FIG. 9, the Optimizer 118, after receiving the current field arrangement (F) and the organ at risk objective functions (OAR) (e.g., average organ at risk dose volume histograms (OAR DVH), mean cohort organ at risk dose volume histograms (OAR DVH), average organ at risk objectives (OAR), which are converted into one or more 2D penalty matrices for the one or more organs at risk) determined previously, may now produce optimized results for a 3D dose distribution (D3D), fluences (Fl) and associated dose volume histograms (DVH) for the patient. Each of these results is stored in the current patient record 112.

Figure 10:
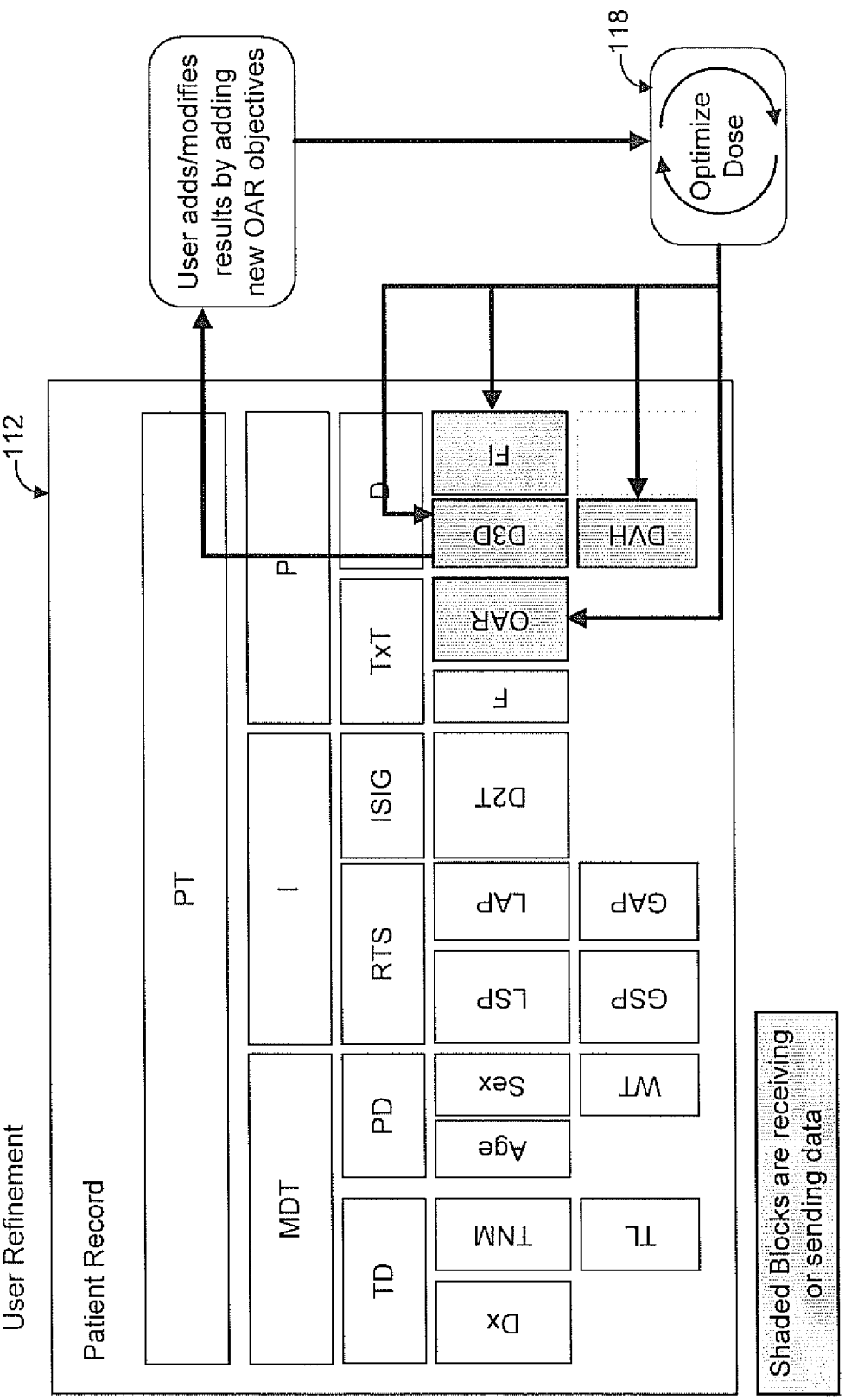

As illustrated in FIG. 10, after the Optimizer 118 produces its optimized results, the clinician is able to review the 3D dose distribution results (D3D) and add additional organ at risk objectives, or adjust existing organ at risk objectives to drive the dose distribution to where the clinician desires it to be. These adjusted organ at risk objectives are applied to the Optimizer 118 which generates an updated set of fluences (Fl) and associated 3D dose distribution (D3D), and an updated dose volume histogram (DVH), which are also applied to the current patient record 112. These changes made by the clinician may also be applied to the existing organ at risk objective (OAR), the average organ at risk dose volume histogram (OAR DVH) and the cohort average organ at risk dose volume histogram (OAR DVH) in the knowledge base 102 to update them based on the changes that the clinician required to reach the desired results. Such changes made by the clinician will allow the radiation therapy treatment planning system 100 to self-learn. In other words, the next time that the clinician uses the system 100, these changes will already exist in the average organ at risk dose volume histogram (OAR DVH) and the cohort average organ at risk dose volume histogram (OAR DVH) for each of the organs at risk. Such clinician-provided final result adjustments can help guide the system over time to get closer to what the clinician desires. In one embodiment, as the results of the radiation therapy treatment planning system 100 improve, the clinician can adjust the OAR objectives, as described above, to produce still more improved results which will in turn aid the system 100 in producing increasingly better results. The average and cohort average dose volume histograms will also improve, allowing for a closer optimal fit right from the start of the process.

Figure 11:
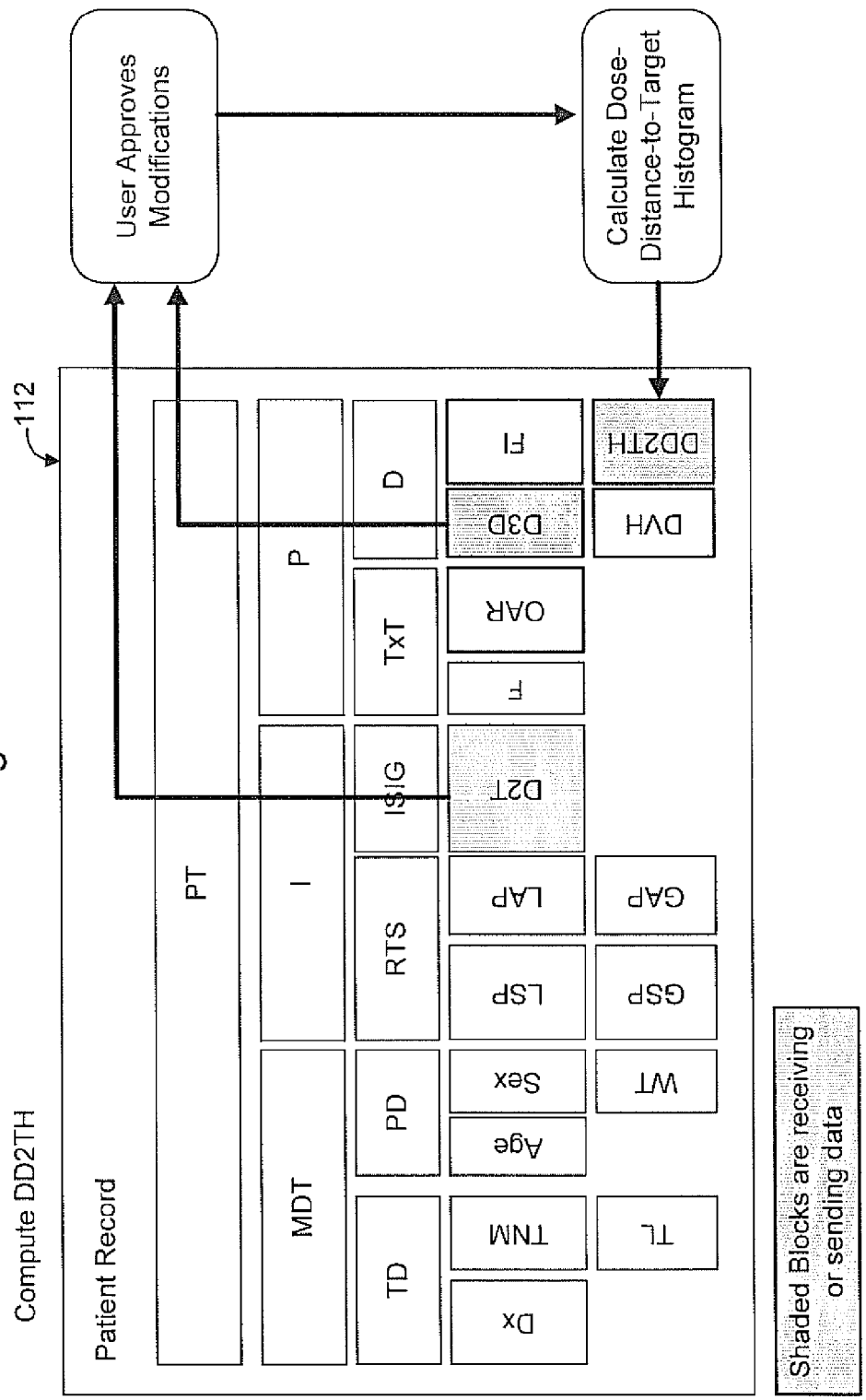

As illustrated in FIG. 11, after the clinician approves the final results of the treatment planning system 100, the distance to target map (D2T) and the 3D dose distribution (D3D) saved in the patient record 112 are used to calculate a dose distance to target histogram (DD2TH) for the current patient. This dose distance to target histogram (DD2TH) is also saved to the patient record 112, completing the record 122.

Figure 12:
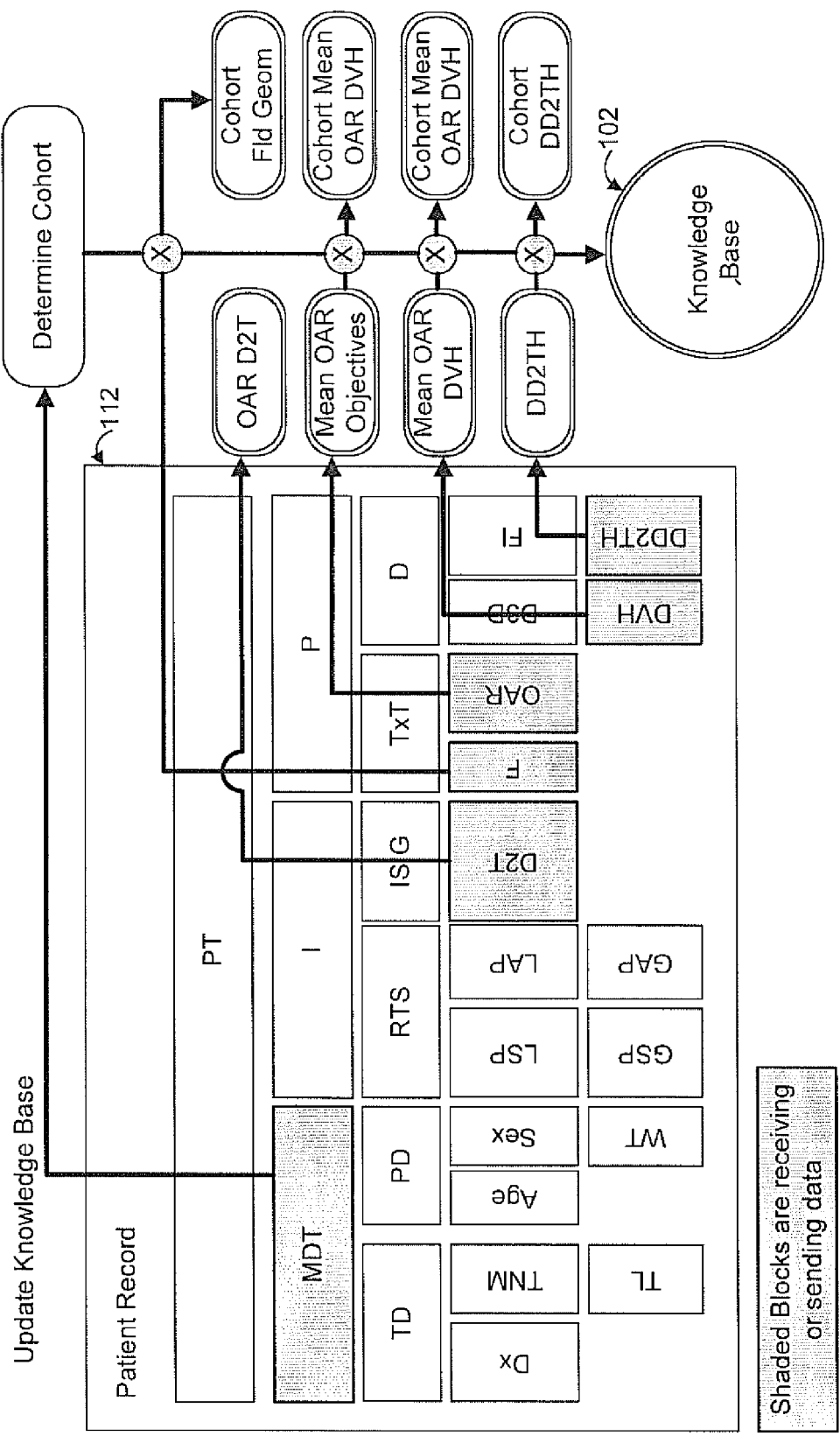

Now that the treatment plan, as contained in the patient record 122, is complete and approved by the clinician, the completed patient record 122 can be saved to the knowledge base 102, which will also allow the population and associated cohorts to be updated as well. Therefore, as illustrated in FIG. 12, after determining which cohort the patient record 122 belongs in (based on the patient record metadata (MDT): disease diagnosis, stage, treatment, etc.), the field geometry for the cohort is updated (saving which field arrangement was used). Updating the cohort with the actual field arrangement used for this particular patient record allows the system to update which field arrangement and treatment type is most popular for a particular set of patient meta data. The population statistics (i.e., the first column of updated values in FIG. 12) and the cohort statistics (i.e., the second column of updated values in FIG. 12) in the knowledge base 102 are updated as well. In other words, the elements of the completed patient record 122 are applied to the average of the knowledge base population as well as to the particular cohort the patient belongs in. Data from the completed patient record 122, applied to the existing data in its cohort, will improve the results for that cohort.

Figure 13:
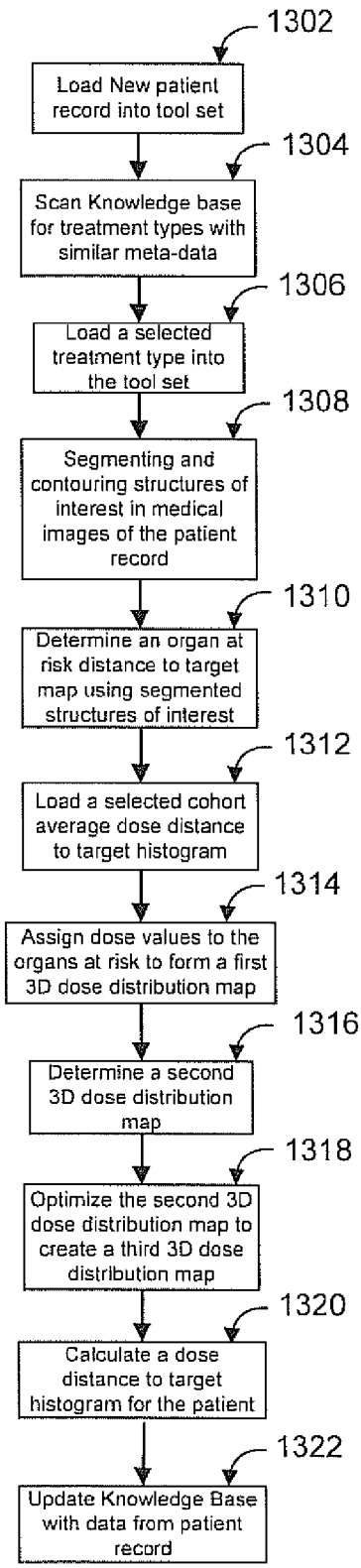
FIG. 13 illustrates steps of an exemplary process for forming a radiation therapy treatment plan, in accordance with an embodiment of the present disclosure.

FIG. 13 illustrates the steps to a method for building a radiation therapy treatment plan with a prescribed radiation therapy dose distribution. In step 1302 a new patient record 112 is loaded into the tool set 110. In step 1304, the knowledge base 102 is scanned for treatment types 106 used by previous patient records 104 with similar meta data (MDT). In step 1306, the selected treatment type 114 is downloaded into the tool set 110. In step 1308, the medical image processing module 116 segments and contours the structures of interest (e.g., organs) in the medical images of the patient record 112.

In step 1310, an organ at risk distance to the target organ map (D2T) is generated using the segmented structures of interest by determining a minimum distance for each pixel of the segmented structures from the target organ. In step 1312, a selected cohort average dose distance to target histogram is downloaded from the knowledge base 102. As shown in FIG. 4, the selected cohort average dose distance to target histogram is selected based on the patient record's meta data (MDT), the calculated distance to target map (D2T), and the selected treatment type 114.

In step 1314, dose values are assigned to the pixels of the organs at risk to form a first 3D dose distribution map. The dose values are derived from the downloaded cohort average dose distance to target histogram. In step 1316, a second 3D dose distribution is determined by the Optimizer 118 based on the field arrangements and the dose distribution in the patient record supplied to the Optimizer 118. In step 1318, based on selected and determined organ at risk objectives (e.g., average organ at risk dose volume histograms, cohort average organ at risk dose volume histograms, which are used to form 2D penalty maps), an optimized 3D dose distribution, associated fluences, and a dose volume histogram are generated by the Optimizer 118 and stored in the patient record 112. In step 1320, after the clinician approves the results of the generated radiation therapy treatment plan, including any additional Optimizer 118 runs based on clinician adjustments to the organ at risk objectives, a dose distance to target histogram is calculated and saved in the patient record 112. Lastly, in step 1322, the data from completed patient record 122 is now saved to the knowledge base 102, thereby updating both the average population statistics and selected cohort population statistics.

Although certain preferred embodiments and methods have been disclosed herein, it will be apparent from the foregoing disclosure to those skilled in the art that variations and modifications of such embodiments and methods may be made without departing from the spirit and scope of the invention. It is intended that the invention shall be limited only to the extent required by the appended claims and the rules and principles of applicable law.

What is claimed is:

1. A method for determining a radiation therapy dose distribution, comprising:
   selecting and downloading a treatment type for a patient from a database;
   determining an organ at risk (OAR) distance to target map, wherein the OAR distance to target map comprises distances to a target organ for respective portions of at least one OAR, and wherein the OAR distances are determined from at least one segmented patient organ image;
   selecting and downloading a cohort average dose distance to target histogram from the database;
   assigning a dose value to each of the portions of the at least one OAR to form a first 3D dose distribution map, wherein the assigned dose values are from the selected cohort average dose distance to target histogram;
   determining a second 3D dose distribution map based on a field arrangement determined by the selected treatment type and the first 3D dose distribution map; and
   calculating a dose distance to target histogram for the patient using the second 3D dose distribution map and the distance to target map.

2. The method of claim 1 further comprising optimizing the second 3D dose distribution map to generate a third 3D dose distribution map, wherein the dose distance to target histogram is calculated using the third 3D dose distribution map.

3. The method of claim 2, wherein optimizing the second 3D dose distribution map uses at least one OAR objective comprising at least one of: an average OAR dose volume histogram, a cohort average OAR dose volume histogram, 2D penalty maps, biological objectives, and a dose distance to target histogram.

4. The method of claim 3, further comprising:
   optimizing the third 3D dose distribution map to generate a fourth 3D dose distribution map using adjusted OAR objectives to drive a dose volume histogram in a desired direction, wherein calculating the dose distance to target histogram uses the fourth 3D dose distribution map and the distance to target map.

5. The method of claim 3, further comprising:
   updating the database, wherein population and cohort populations are updated with current patient information, and wherein updating the database comprises updating the plurality of OAR objectives.

6. The method of claim 1, wherein the selected cohort average dose distance to target histogram is based on a patient's meta-data, the selected treatment type, and the OAR distance to target map.

7. The method of claim 6, wherein the selected cohort average OAR dose volume histogram has an average distance to target for the OAR that is similar to the average distance to target for the OAR of the patient.

8. The method of claim 6, wherein the cohort average dose distance to target histogram is an average of a plurality of dose distance to target histograms of radiation therapy dose distribution plans with similar meta-data and organ at risk distance to target maps.

9. The method of claim 1, wherein the portions of a plurality of organs at risk comprise individual pixels.

10. The method of claim 1, wherein the distance to the target organ is the shortest distance to the target organ.

11. The method of claim 1, wherein the selection of the treatment type is based on a patient's meta-data.

12. The method of claim 10, wherein the treatment type selected is the most frequently selected treatment type for the meta-data.

13. The method of claim 1, wherein the OAR distance to target map is determined from structure sets in a medical image, and wherein the structure sets are determined after segmentation of the medical image is complete.

14. The method of claim 1, wherein the selected cohort average dose distance to target histogram has a confidence level greater than a desired confidence level.

15. The method of claim 2, wherein optimizing the second 3D dose distribution map utilizes an optimizer that takes the field arrangements and the first 3D dose distribution map and calculates a set of fluences that provide the third 3D dose distribution map.

16. A computer readable, non-transitory storage media having computer-readable and computer-executable instructions embodied therein for causing a computer system to execute a method for determining a radiation therapy dose distribution, the computer-executable instructions comprising:
   instructions to select and download a treatment type for a patient from a database;
   instructions to determine an organ at risk (OAR) distance to target map, wherein the OAR distance to target map comprises distances to a target organ for respective portions of at least one OAR, and wherein the OAR distances are determined from at least one segmented patient organ image;
   instructions to select and download a cohort average dose distance to target histogram from the database;
   instructions to assign a dose value to each of the portions of the at least one OAR to form a first 3D dose distribution map, wherein the assigned dose values are from the selected cohort average dose distance to target histogram;
   instructions to determine a second 3D dose distribution map based on a field arrangement determined by the selected treatment type and the first 3D dose distribution map; and
   instructions to calculate a dose distance to target histogram for the patient using the second 3D dose distribution map and the distance to target map.

17. The method of claim 16 further comprising instructions to optimize the second 3D dose distribution map to generate a third 3D dose distribution map, wherein the dose distance to target histogram is calculated using the third 3D dose distribution map.

18. The method of claim 17, wherein optimizing the second 3D dose distribution map uses at least one OAR objective comprising at least one of: an average OAR dose volume histogram, a cohort average OAR dose volume histogram, 2D penalty maps, biological objectives, and a dose distance to target histogram.

19. The method of claim 18, the computer-executable instructions further comprising:
   instructions to optimize the third 3D dose distribution map to generate a fourth 3D dose distribution map using adjusted OAR objectives to drive a dose volume histogram in a desired direction, wherein calculating the dose distance to target histogram uses the fourth 3D dose distribution map and the distance to target map.

20. The method of claim 18, the computer-executable instructions further comprising:
   instructions to update the database, wherein population and cohort populations are updated with current patient information, and wherein updating the database comprises updating the plurality of OAR objectives.

21. The method of claim 16, wherein the selected cohort average dose distance to target histogram is based on a patient's meta-data, the selected treatment type, and the OAR distance to target map.

22. The method of claim 21, wherein the selected cohort average OAR dose volume histogram has an average distance to target for the OAR that is similar to the average distance to target for the OAR of the patient.

23. The method of claim 21, wherein the cohort average dose distance to target histogram is an average of a plurality of dose distance to target histograms of radiation therapy dose distribution plans with similar meta-data and organ at risk distance to target maps.

24. The method of claim 16, wherein the portions of a plurality of organs at risk comprise individual pixels.

25. The method of claim 16, wherein the distance to the target organ is the shortest distance to the target organ.

26. The method of claim 16, wherein the selection of the treatment type is based on a patient's meta-data.

27. The method of claim 25, wherein the treatment type selected is the most frequently selected treatment type for the meta-data.

28. The method of claim 16, wherein the OAR distance to target map is determined from structure sets in a medical image, and wherein the structure sets are determined after segmentation of the medical image is complete.

29. The method of claim 16, wherein the selected cohort average dose distance to target histogram has a confidence level greater than a specified level of confidence.

30. The method of claim 17, wherein optimizing the second 3D dose distribution map utilizes an optimizer that takes the field arrangements and the first 3D dose distribution map and calculates a set of fluences that provide the third 3D dose distribution map.

* * * * *